United States Patent
Simanzhenkov et al.

(10) Patent No.: US 10,406,517 B2
(45) Date of Patent: *Sep. 10, 2019

(54) DOUBLE PEROXIDE TREATMENT OF OXIDATIVE DEHYDROGENATION CATALYST

(71) Applicant: NOVA Chemicals (International) S.A., Fribourg (CH)

(72) Inventors: Vasily Simanzhenkov, Calgary (CA); Xiaoliang Gao, Calgary (CA); David Jeffrey Sullivan, Calgary (CA); Hanna Drag, Calgary (CA); Marie Barnes, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/839,947

(22) Filed: Dec. 13, 2017

(65) Prior Publication Data

US 2018/0193827 A1   Jul. 12, 2018

(51) Int. Cl.
| | |
|---|---|
| *B01J 23/00* | (2006.01) |
| *B01J 37/00* | (2006.01) |
| *B01J 37/06* | (2006.01) |
| *B01J 37/08* | (2006.01) |
| *B01J 37/12* | (2006.01) |

(52) U.S. Cl.
CPC ............ *B01J 37/12* (2013.01); *B01J 23/002* (2013.01); *B01J 23/28* (2013.01); *B01J 27/0576* (2013.01);
(Continued)

(58) Field of Classification Search
CPC .......... B01J 37/009; B01J 37/06; B01J 37/08; B01J 37/12; B01J 23/002; C07C 5/3332; C07C 2523/28
See application file for complete search history.

(56) References Cited

U.S. PATENT DOCUMENTS

| | | | |
|---|---|---|---|
| 2,895,920 A | 7/1959 | Janoski | |
| 3,474,042 A | 10/1969 | Fattore et al. | |

(Continued)

FOREIGN PATENT DOCUMENTS

RU   2358958 C1 *  6/2009   ............. B01J 37/04

OTHER PUBLICATIONS

Sanchez Sanchez, Maricruz; Girgsdies, Frank; Justak, Mateusz; Kube, Pierre; Schlogl, Robert and Trunschke, Annette; Aiding the Self-Assembly of Supramolecular Polyoxometalates under Hydrothermal Conditions to Give Precursors of Complex Functional Oxides; Copyright 2012 by Wiley-VCH Verlag GmbH & Co.; Angewandte Chemie; Int. Ed. 2012, 51, pp. 7194-7197.

(Continued)

*Primary Examiner* — Jun Li
(74) *Attorney, Agent, or Firm* — Lawrence T. Kale

(57) ABSTRACT

Oxidative dehydrogenation catalysts comprising MoVNbTeO having improved consistency of composition and a 25% conversion of ethylene at less than 420° C. and a selectivity to ethylene above 95% are prepared by treating the catalyst precursor with $H_2O_2$ in an amount equivalent to 0.30-2.8 mL $H_2O_2$ of a 30% solution per gram of catalyst precursor prior to calcining and treating the resulting catalyst with the equivalent amount of peroxide after calcining.

11 Claims, 11 Drawing Sheets

(51) Int. Cl.

| | | |
|---|---|---|
| *C07C 5/333* | (2006.01) | |
| *B01J 37/03* | (2006.01) | |
| *B01J 37/04* | (2006.01) | |
| *B01J 37/10* | (2006.01) | |
| *B01J 23/28* | (2006.01) | |
| *B01J 27/057* | (2006.01) | |
| *B01J 35/00* | (2006.01) | |
| *C07C 5/48* | (2006.01) | |
| *B01J 35/10* | (2006.01) | |

(52) U.S. Cl.
CPC ........ *B01J 35/006* (2013.01); *B01J 37/009* (2013.01); *B01J 37/031* (2013.01); *B01J 37/04* (2013.01); *B01J 37/06* (2013.01); *B01J 37/08* (2013.01); *B01J 37/088* (2013.01); *B01J 37/10* (2013.01); *C07C 5/3332* (2013.01); *C07C 5/48* (2013.01); *B01J 35/002* (2013.01); *B01J 35/1009* (2013.01); *B01J 35/1014* (2013.01); *B01J 37/0009* (2013.01); *B01J 2523/00* (2013.01); *C07C 2523/20* (2013.01); *C07C 2523/22* (2013.01); *C07C 2523/28* (2013.01); *C07C 2527/057* (2013.01); *Y02P 20/52* (2015.11)

(56) References Cited

U.S. PATENT DOCUMENTS

| | | | |
|---|---|---|---|
| 4,709,070 A | 11/1987 | Sasaki et al. | |
| 7,304,014 B2 * | 12/2007 | Cavalcanti | B01J 23/002 502/300 |
| 8,105,972 B2 | 1/2012 | Gaffney et al. | |
| 2004/0029725 A1 * | 2/2004 | Gaffney | B01J 23/002 502/208 |
| 2005/0239643 A1 * | 10/2005 | Benderly | B01J 23/002 502/312 |
| 2007/0004584 A1 * | 1/2007 | Kobayashi | B01J 23/002 502/60 |
| 2008/0161602 A1 * | 7/2008 | Wang | B01J 23/002 562/549 |
| 2008/0194871 A1 * | 8/2008 | Dubois | B01J 23/002 562/549 |
| 2008/0249328 A1 * | 10/2008 | Kaduk | B01J 23/002 558/321 |
| 2009/0042723 A1 * | 2/2009 | Wang | B01J 23/002 502/312 |
| 2011/0178333 A1 * | 7/2011 | Kim | B01J 23/002 562/549 |
| 2017/0050178 A1 * | 2/2017 | Simanzhenkov | C07C 5/48 |
| 2019/0039053 A1 * | 2/2019 | Kim | C07C 5/48 |

OTHER PUBLICATIONS

Wen, C.Y. and Yu, Y.H.; Mechanics of Fluidization; Fluid Particle Technology, Chemical Engineering Progress Symposium Series, 1964-1965; No. 62, vol. 62; pp. 100-111.

Peri, J.B. and Hensley, A.L., Jr.; The Surface Structure of Silica Gel; The Journal of Physical Chemistry, Aug. 1968, vol. 72, No. 8; pp. 2926-2933.

* cited by examiner

DOUBLE PEROXIDE TREATMENT OF OXIDATIVE DEHYDROGENATION CATALYST

FIELD OF THE INVENTION

The present disclosure relates to an improved method for making a catalyst for the oxidative dehydrogenation of lower alkanes to lower alkenes. Multi-component metal oxide catalysts for the oxidative dehydrogenation of alkanes are known. Such catalysts are typically made by mixing solutions of metals and then precipitating the metal oxide "mixture" from the solution and calcining it. As a result the catalysts are heterogeneous mixtures of various metal oxides and phases and may include some highly active species but also some species which have a significantly lower activity. Applicants have found that by treating the precipitated metal oxides with a controlled amount of hydrogen peroxide prior and subsequent to calcining, both the consistency and activity of the catalyst is improved.

BACKGROUND

U.S. Pat. No. 2,895,920 issued Jul. 21, 1959 to Janoski, assigned to Sun Oil Company teaches a process to prepare a catalyst for the conversion of hydrocarbons such as dehydrogenation. The catalysts comprise oxides of cobalt, iron, nickel, molybdenum, manganese, chromium, vanadium, tin, and tungsten. The catalysts do not incorporate any niobium. In the process to make the catalysts a hydrogel is prepared of metal oxide(s) which are difficult to reduce and metal oxides which are capable of existing in several oxidation states. A hydrogel of the metals is prepared and aged in the presence of hydrogen peroxide. The aged hydrogel is treated with a compound to precipitate the metals which are then filtered, dried and calcined. The sequence of treatments is different than that in the present invention.

U.S. Pat. No. 3,474,042 issued Oct. 21, 1969 to Fattore et al., assigned to Montecatini Edison S.p.A. teaches a metal oxide catalyst comprising molybdenum or tungsten. The catalysts are prepared by forming peroxy—compounds of tungsten and molybdenum, by reacting the metal oxide with hydrogen peroxide or compounds which form hydrogen peroxide. The molar ratio of peroxide to metal oxide may range from 0.25 to 10, typically from 1 to 3. The solution may be spray-dried or impregnated into a carrier.

U.S. Pat. No. 4,709,070 issued Nov. 24, 1987 to Sasaki et al., assigned to Nitto Chemical industry Co., Ltd. teaches a method to regenerate the activity of a complex metal oxide catalyst used for oxidation, ammoxidation and oxidative dehydrogenation of alkanes. The catalysts prior to reactivation are quite different from those herein. They contain a number of elements not present in the catalysts of the present invention such as Fe, Sb, Cu, and Co. The "deactivated" catalyst is treated with a Te compound, a Mo compound or a mixture thereof. The Te and Mo compounds may be oxides. In some instances the Te and Mo compounds may be prepared by contacting them with $H_2O_2$ in the presence of the oxide, oxyacid, salts of oxyacids, heteropoly acids or salts thereof of molybdenum (Col. 9 lines 38-42). The patent teaches away from treating the entire catalyst precursor and resulting catalyst with $H_2O_2$.

The supporting data for "Aiding the Self-Assembly of Supramolecular Polyoxometalates Under Hydrothermal Conditions to Give Precursors of Complex Functional Oxides", *Angewandte Chemie* 201200746, Maricruz Sanchez, Frank Girgsdies, Mateusz Jastak, Pierre Kube, Robert Schlogo and Annette Trunschke (copyright Wiley—VCH 2012) teaches a hydrothermal process for making complexes similar to oxidative dehydrogenation catalysts. The components are added step wise to the autoclave apparently without reducing pressure. The addition of components is monitored by Raman spectroscopy to provide a product having a high amount of M1 phase without peroxide treatment. The reference does not suggest treating the intermediate or the final catalyst with hydrogen peroxide. Complexes produced by the process had the formula $Mo_1V_{0.2}Te_{0.2}Nb_{0.2}O_d$. The reference does not teach the process or the catalysts disclosed hereinafter.

U.S. Pat. No. 8,105,972 issued Jan. 31, 2012 to Gaffney et al. from an application filed Apr. 2, 2009, assigned to Lummus Technology Inc. teaches a catalyst for the oxidative dehydrogenation of alkanes. The catalyst is formed in a conventional manner by hydrothermal treatment of metal oxide components. The resulting catalyst is recovered, dried and calcined. Then the calcined catalyst is treated with an acid. This process teaches away from the subject matter of the present invention as it teaches a post calcining treatment. Further the patent fails to teach treatment with $H_2O_2$.

The present disclosure provides an improved catalyst for oxidative dehydrogenation by treating the catalyst precursor with $H_2O_2$, prior to calcining and the resulting calcined catalyst with $H_2O_2$.

SUMMARY OF THE INVENTION

In one embodiment of this disclosure, an oxidative dehydrogenation catalyst is prepared by the hydrothermal reaction of compounds of Mo, V, Te, and Nb and, prior and subsequent to calcining, treating the precursor and calcined catalyst with $H_2O_2$.

In one embodiment, this disclosure provides an oxidative dehydrogenation catalyst of the empirical formula (measured by PIXE).

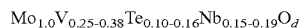

$$Mo_{1.0}V_{0.25-0.38}Te_{0.10-0.16}Nb_{0.15-0.19}O_d$$

where d is a number to satisfy the valence of the oxide.

In one embodiment, this disclosure involves treating a oxidative dehydrogenation catalyst precursor, prior to calcining, with $H_2O_2$ in an amount equivalent to 0.30-2.8 mL $H_2O_2$ of a 30% solution per gram of catalyst precursor and treating the calcined oxidative dehydrogenation catalyst with $H_2O_2$ in an amount equivalent to 0.30-2.8 mL $H_2O_2$ of a 30% solution per gram of catalyst.

In a further embodiment, the catalyst is prepared by:
i) forming an aqueous solution of ammonium heptamolybdate (tetrahydrate) and telluric acid at a temperature from 30° C. to 85° C. and adjusting the pH of the solution to from 6.5 to 8.5, preferably from 7 to 8, most preferably from 7.3 to 7.7 with a nitrogen-containing base to form soluble salts of the metals;
ii) preparing an aqueous solution of vanadyl sulphate at a temperature from room temperature to 80° C. (preferably 50° C. to 70° C., most preferably 55° C. to 65° C.);
iii) mixing the solutions from steps i) and ii) together;
iv) slowly (dropwise) adding a solution of niobium monoxide oxalate ($NbO(C_2O_4H)_3$) to the solution of step iii) to form a slurry;
v) heating the resulting slurry in an autoclave under an inert atmosphere at a temperature from 150° C. to 190° C. for not less than 10 hours (hydrothermal treatment);
vi) treating either:
a) the resulting slurry with the equivalent of from 0.3-2.8 mL of a 30% w/w solution of $H_2O_2$ per gram of catalyst precursor for a time from 5 minutes to 10 hours at a temperature from 20 to 80° C. and filtering and drying the resulting solid; or b) filtering and washing with deionized water, and drying the washed solid from step v) for a time from 4 to 10 hours at a temperature from 70 to 100° C. treating the dried isolated precursor, with the equivalent of from 0.3-2.8 mL of a 30% w/w solution of $H_2O_2$ per gram of catalyst precursor for a time from 5 minutes to 10 hours at a temperature from 20 to 80° C.;

vii) calcining the resulting precursor in an inert atmosphere at a temperature from 200° C. to 600° C. for a time from 1 to 20 hours;

viii) recovering the calcined catalyst from step vii) and treating it with the equivalent of 0.3-2.8 mL of a 30% w/w solution of $H_2O_2$ per gram of calcined catalyst for a time from 5 minutes to 10 hours at a temperature from 20 to 80° C.; and ix) recovering the treated calcined catalyst.

In a further embodiment in the catalyst the molar ratio of Mo:V is from 1:0.26 to 1:0.38.

In a further embodiment in the catalyst, the molar ratio of Mo:Te is greater than 1:0.11 and less than 1:0.15.

In a further embodiment in the catalyst, the molar ratio of Mo:Te is from 1:0.11 to 1:0.13.

In a further embodiment in the catalyst, the molar ratio of Mo:Nb is from 1:0.11 to 1:0.16.

In a further embodiment, the catalyst has a bulk density from 1.20 to 1.53 g/cc.

In a further embodiment in the crystalline phase of the catalyst, the amount of the phase having the formula $(TeO)_{0.39}(Mo_{3.52}V_{1.06}Nb_{0.42})O_{14}$ is above 75 wt % of the measured crystalline phase as determined by XRD.

In a further embodiment, the active phase of the catalyst after double hydrogen peroxide treatment has an XRD peak at 21.81 (±0.4) which is apparent and not hidden in the reference reflection at 22.29 (±0.4).

A further embodiment, the active phase of the double $H_2O_2$ treated catalyst has an XRD height at 21.81 (±0.4) 2θ which is 1-6% relative peak height of the reference reflection at 22.29 (±0.4) 2θ.

A further embodiment, of this disclosure provides a method for the oxidative dehydrogenation of a mixed feed of ethane and oxygen in a volume ratio from 70:30 to 95:5 at a temperature less than 425° C., preferably less than 400° C. preferably less than 390° C. at a gas hourly space velocity of not less than 500 hr$^{-1}$ and a pressure from 0.8 to 1.2 atmospheres comprising passing said mixture over the above catalyst.

In a further embodiment, a conversion to ethylene is not less than 90%.

In a further embodiment the gas hourly space velocity is not less than 1000 hr$^{-1}$.

In a further embodiment, the calcined catalyst forms a fixed bed in the reactor.

In a further embodiment, the catalyst has the empirical formula (measured by PIXE):

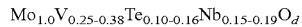

$Mo_{1.0}V_{0.25-0.38}Te_{0.10-0.16}Nb_{0.15-0.19}O_d$ where d is a number to satisfy the valence of the oxide.

In a further embodiment, the hydrothermal reactor is seeded with the above double peroxide treated catalyst.

In a further embodiment, the internal surface of the hydrothermal reactor is selected from the group consisting of stainless steel, silica, alumina coating and polytetrafluoroethylene.

In a further embodiment, the hydrothermal reactor contains particulates (irregular such as flakes, granules, globules, filaments, etc. or regular such as spheres, elliptical, rods, rectangular prisms (both right and non-right), pentagonal prisms, pyramids, etc.) of stainless steel, silica, glass (e.g. PYREX®—borosilicate glass) alumina and polytetrafluoroethylene seeded with the above double peroxide treated catalyst.

In a further embodiment, there is provided a fully fluorinated ethylene propylene polymer reactor coating seeded with the above double peroxide treated catalyst.

DETAILED DESCRIPTION

Numbers Ranges

Figure 1:
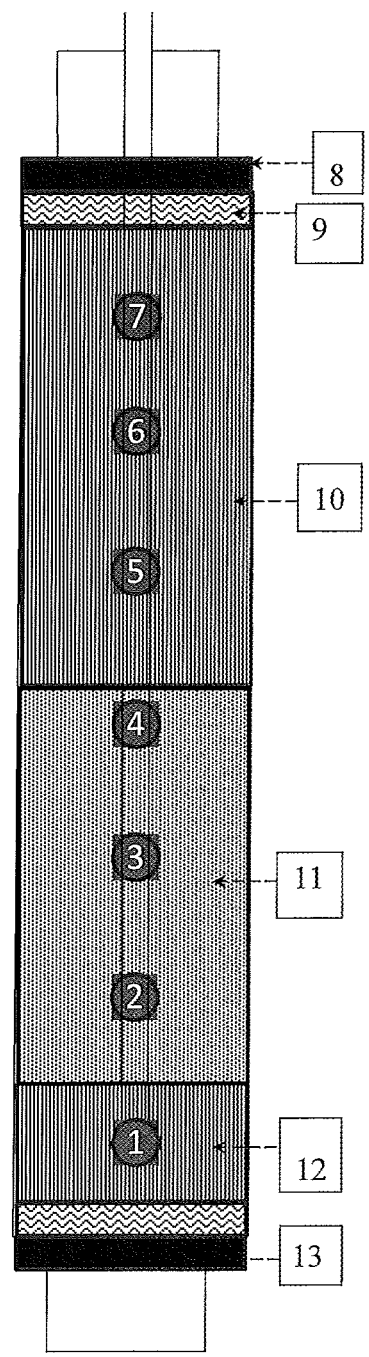
FIG. 1 is a schematic drawing of the reactor used for testing the ODH catalysts.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the properties that the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of this disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, the amounts of the components actually used will conform to the maximum of 100 percent.

In the specification, the phrase the temperature at which there is 25% conversion of ethane to ethylene is determined by determining conversion at a number of temperatures typically with data points below and above 25% conversion. Then a plot of the data is prepared or the data is fit to an equation and the temperature at which there is a 25% conversion of ethane to ethylene is determined.

In the specification, the phrase selectivity at 25% conversion is determined by determining the selectivity at a number of temperatures below and above the temperature for 25% conversion. The data may then be plotted or fit to an equation. Then having calculated the temperature at which 25% conversion occurs one can determine either from the graph or from the equation the selectivity at that temperature.

The calcined catalysts of the present invention typically have the formula (as determined by PIXE):

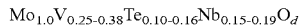

$$Mo_{1.0}V_{0.25-0.38}Te_{0.10-0.16}Nb_{0.15-0.19}O_d$$

where d is a number to satisfy the valence of the oxide. In some embodiments the molar ratio of Mo:V in the calcined catalyst is from 1:0.25 to 1:0.35, in other embodiments the molar ratio of Mo:V in the calcined catalyst is from 1:0.27 to 1:0.32, in some embodiments from 1:0.28 to 1:0.30. In other embodiments the molar ratio of Mo:Te in the calcined catalyst is greater than 1:0.10 and less than 1:0.16, in further embodiments the molar ratio of Mo:Te in the calcined catalyst is from 1:0.11 to 1:0.15.

The catalyst is typically prepared by mixing solutions or slurries (suspensions) of oxides or salts of the metallic components.

In some embodiments the catalyst may be prepared by a process comprising the following steps:

i) forming an aqueous solution of ammonium heptamolybdate (tetrahydrate) and telluric acid at a temperature from 30° C. to 85° C. and adjusting the pH of the solution to 6.5 to 8.5, preferably from 7 to 8, most preferably from 7.3 to 7.7 preferably with a nitrogen-containing base to form soluble salts of the metals;

ii) preparing a aqueous solution of vanadyl sulphate at a temperature from room temperature to 80° C. (preferably 50° C. to 70° C., most preferably 55° C. to 65° C.);

iii) mixing the solutions from steps i) and ii) together;

iv) slowly (dropwise) adding a solution of niobium monoxide oxalate (NbO(C$_2$O$_4$H)$_3$) to the solution of step iii) to form a slurry;

v) heating the resulting slurry in an autoclave under an inert atmosphere at a temperature from 150° C. to 190° C. for not less than 10 hours (hydrothermal treatment);

vi) filtering and washing the slurry from step v) with deionized water and drying the resulting solid for a time from 4 to 10 hours at a temperature from 70 to 100° C.;

vii) treating the dried precursor from step vi with the equivalent of from 0.3-2.8 mL of a 30% w/w solution of H$_2$O$_2$ per gram of catalyst precursor for a time from 5 minutes to 10 hours at a temperature from 20 to 80° C.;

viii) calcining the resulting catalyst precursor in an inert atmosphere at a temperature from 200° C. to 600° C. for a time from 1 to 20 hours;

ix) recovering the calcined catalyst from step viii) and treating it with the equivalent of from 0.3-2.8 mL of a 30% w/w solution of H$_2$O$_2$ per gram of calcined catalyst for a time from 5 minutes to 10 hours at a temperature from 20 to 80° C.; and x) recovering the treated calcined catalyst.

Following step i) one or more of the following steps may be incorporated in the process:

a) evaporating the aqueous solvent to obtain a solid;

b) drying the solid at a temperature from 80° C. to 100° C.; and c) redissolving the solid in water at a temperature from 40° C. to 80° C. (preferably 50° C. to 70° C., most preferably 55° C. to 65° C.).

Following step ii) the solutions may be cooled to a temperature from 20° C. to 30° C.

As a part of step vi) the solution may be cooled to a temperature from 20° C. to 30° C.

In a further embodiment, the precursor may be made by a process comprising:

i) forming an aqueous solution of ammonium heptamolybdate (tetrahydrate) and telluric acid at a temperature from 30° C. to 85° C. and adjusting the pH of the solution to 7.3 to 7.7 (preferably 7.4 to 7.5) with a nitrogen-containing base to form soluble salts of the metals;

ii) evaporating the aqueous solvent to obtain a solid;

iii) drying the solid at a temperature from 80° C. to 100° C.;

iv) redissolving the solid in water at a temperature from 40° C. to 80° C. (preferably 50° C. to 70° C., most preferably 55° C. to 65° C.);

v) preparing a aqueous solution of vanadyl sulphate at a temperature from room temperature to 80° C. (preferably 50° C. to 70° C., most preferably 55° C. to 65° C.);

vi) cooling the solutions from steps iv) and v) to a temperature from 20 to 30° C.;

vii) mixing the cooled solutions from step vi together;

viii) slowly (dropwise) adding a solution of niobium monoxide oxalate (NbO(C$_2$O$_4$H)$_3$) to the solution of step vii) to form a (brown) slurry;

ix) heating the resulting slurry in an autoclave under an atmosphere free of oxygen at a temperature from 150° C. to 190° C. for not less than 10 hours;

x) cooling the autoclave to room temperature and filtering and washing with deionized water the resulting solid; and xi) drying the washed solid for a time from 4 to 10 hours at a temperature from 70 to 100° C.

In some embodiments, the (hydrothermal) reactor may be lined with a coating selected from the group consisting of stainless steel, silica, alumina coating and polytetrafluoroethylene, preferably polytetrafluoroethylene (TEFLON®) seeded with catalyst having a 25% conversion to ethylene at 420° C. or less and a selectivity to ethylene of not less than 90%.

The seed catalyst may be a catalyst having the empirical formula (measured by PIXE):

$$Mo_{1.0}V_{0.25-0.38}Te_{0.10-0.16}Nb_{0.15-0.19}O_d$$

where d is a number to satisfy the valence of the oxide and having not less than 75 wt % of a crystalline component of the formula $(TeO)_{0.39}(Mo_{3.52}V_{1.06}Nb_{0.42})O_{14}$ as determined by XRD.

The (hydrothermal) reactor may be lined with a coating of a fully fluorinated ethylene propylene polymer (FEP) seeded with a catalyst having a 25% conversion to ethylene at 380° C. or less and a selectivity to ethylene of not less than 90% at a gas hourly space velocity of not less than 500 hr$^{-1}$. The seed catalyst may have the empirical formula (measured by PIXE) $Mo_{1.0}V_{0.25-0.38}Te_{0.10-0.16}Nb_{0.15-0.19}O_d$ where d is a number to satisfy the valence of the oxide. Typically not less than 75 wt % of a crystalline component of the seed catalyst has the formula $(TeO)_{0.39}(Mo_{3.52}V_{1.06}Nb_{0.42})O_{14}$ as determined by XRD.

The seed catalyst loadings may range from 1 to 15 wt % of the surface of the hydrothermal reactor (e.g. steel, TEFLON or FEP).

In some instances the (hydrothermal) reactor contains particulates of stainless steel, silica, alumina and polytetrafluoroethylene seeded with a catalyst having a 25% conversion to ethylene at 420° C. or less and a selectivity to ethylene of not less than 90% such as that described above.

The particulates may be (irregular such as flakes, granules, globules, filaments, etc. or regular such as spheres, elliptical, rods (stirring bars), rectangular prisms (both right and non-right), pentagonal prisms, pyramids, etc.)

In some circumstances, it may be easier to replace particulates on which the seed catalyst has, for whatever reason, been depleted with new seed particles having an appropriate loading of seed particles than to replenish the seed coating on the interior surface of the catalyst reactor.

A catalyst produced from a hydrothermal reactor seeded with catalyst having a 25% conversion to ethylene at 380° C. or less and a selectivity to ethylene of not less than 90% generally has the empirical formula as determined by PIXE $Mo_1V_{0.25-0.35}Te_{0.10-0.16}Nb_{0.15-0.19}O_d$ where d is a number to satisfy the valence of the oxide.

The peroxide treatments may take place at atmospheric pressure and room temperature (e.g. from 15° C. to 30° C.) to about 80° C., in some instances from 35° C. to 75° C. in other instances from 40° C. to 65° C. The peroxide has a concentration from 10 to 30 wt %, in some instances from 15 to 25 wt %. The treatment time may range from 1 to 10 hours, in some cases from 2 to 8 hours, in other cases from 4 to 6 hours.

The catalyst precursor is treated with the equivalent of from 0.3-2.8, in some embodiments from 0.3-2.5 mL of a 30 wt % solution of aqueous $H_2O_2$ per gram of precursor. The treatment should be in a slurry (e.g. the precursor is at least partially suspended) to provide an even distribution of $H_2O_2$ and to control the temperature rise. In some cases the peroxide may be added directly to the slurry obtained from the hydro thermal reactor while in other cases the product from the hydrothermal reactor may be recovered, (filtered) washed, dried and re-slurried and then treated with the peroxide.

The process of the present disclosure is an instantaneous reaction (i.e. there is no delay before the reaction starts) which is more controlled and safer.

The treated catalyst precursor is then subject to calcining to produce the active oxidative dehydrogenation catalyst. The treated precursor may be calcined in an inert atmosphere at a temperature from 200° C. to 600° C. for a time from 1 to 20 hours. The purge gases used for calcining are inert gases, including one or more of nitrogen, helium, argon, $CO_2$ (preferably high purity>90%), said gases or mixture containing less than 1 vol.-% hydrogen or air, at 200-600° C., preferably at 300-500° C. The calcining step may take from 1 to 20, in some instances from 5 to 15 in other instances from about 8 to 12 hours, generally about 10 hours. The resulting mixed oxide catalyst is a friable solid typically insoluble in water. Typically the calcined product has a bulk density from 1.20 to 1.53 g/cc. This bulk density is based on how much 1.5 ml of pressed and crushed catalyst weighs.

The calcined catalyst is then redistributed in water and treated with the equivalent of from 0.3-2.8, in some embodiments from 0.3-2.5 mL of a 30 wt % solution of aqueous $H_2O_2$ per gram of catalyst. The treatment is in a slurry or precipitate (e.g. the precursor is at least partially suspended) to provide an even distribution of $H_2O_2$ and to control the temperature rise. This may be achieved by stirring the mixture. The time of treatment may be from about 1 to about 10 hours, typically form 2 to 8 hours in some embodiment from 3 to 7 hours.

The resulting twice treated oxidative dehydrogenation catalyst is then recovered, typically by filtration and optionally washed with deionized water and dried in an oven, at low temperatures, typically from about 30° C. to 90° C. The catalyst is then cooled to room temperature. The resulting catalyst may optionally be and ground to a particle size from about 200 µm to 500 µm, typically from about 200 µm to about 300 µm.

The resulting oxidative dehydrogenation catalyst is heterogeneous. It has an amorphous component and a crystalline component. The elemental analysis of the catalyst may be determined by any suitable technique. One useful technique is Particle Induced X-Ray Emission analysis (PIXE).

The catalyst has one or more crystalline components and an amorphous component. The crystalline component may be analyzed using X-Ray diffraction (XRD). There are a number of suppliers of X-Ray diffractometers including Rigaku Shimadzu, Olympus and Bruker. A powder sample is irradiated with X-Rays. The X-Rays given off from the sample pass through a diffraction grid and are collected in a goniometer (recorder). The results are typically analyzed using a computer program (typically provided by the instrument supplier) and compared to a data base (International Center for Diffraction Data ICDD) using a computer to determine the composition of the crystalline phase(s).

The crystalline phase of the catalyst is also heterogeneous. The X-Ray diffraction results may be analyzed by computer programs to identify various likely crystalline species and their relative amounts compared to the structures in a data base (e.g. deconvoluted).

The crystalline phase typically includes the following crystalline species:
$(Mo_{0.6}Nb_{0.22}V_{0.18})_5O_{14}$;
$TeO_{0.71}(Mo_{0.73}V_{0.2}Nb_{0.07})_3O_9$;
$(TeO)_{0.39}(Mo_{3.52}V_{1.06}Nb_{0.42})O_{14}$;
$V_{1.1}Mo_{0.9}O_5$; $Mo_4V_6O_{25}$; and
$VOMoO_4$ X-Ray diffraction analysis of the precursor and the calcined catalyst shows treatment results in a change in the composition of the crystalline phase. The treatment in accordance with the present disclosure increases the phase of the crystalline component having the empirical formula $(TeO)_{0.39}(Mo_{3.52}V_{1.06}Nb_{0.42})$ to not less than 75 wt %, in some instances not less than 85 wt %.

In some embodiments, the phase of the crystalline component having the empirical formula $TeO_{0.71}(Mo_{0.73}V_{0.2}Nb_{0.07})_3O_9$ is present in an amount of from about 2.4 to 12 wt %, in some embodiments the phase is present in amounts less than about 8 wt %, in further embodiments less than 3.5 wt %.

The ODH catalyst twice treated with hydrogen peroxide has an XRD pattern where the reflection at 21.81° (±0.4°) 2θ is 1-6% in some embodiments from 2 to 6% relative peak height of the reference reflection at 22.29° (±0.4°) 2θ.

In a further embodiment, ODH catalyst twice treated with hydrogen peroxide has an XRD pattern where the reflection at 22.29° (±0.4°) 2θ has a full width at half maximum (FWHM) less than 0.185° 2θ.

Generally, the ODH catalyst twice treated with hydrogen peroxide has a crystallite size (i) greater than 85 Å up to 120, in some case up to 115 calculated using the Scherrer equation, where K (dimensionless shape factor) is assumed to be 1, λ is the X-ray wavelength from Copper source and is 1.5406 Å, θ is the Bragg angle of 22.29°, and β is the line broadening at half the maximum intensity (FWHM) as determined for the XRD data.

The calcined catalyst product is a dry friable product typically insoluble in water. If required the catalyst may be subject to a sizing step, such as grinding, to produce a desired particle size. Depending on how the catalyst is to be used the particle size may be different. For example for spray drying with a support the particle size may range from about 5 to 75 μm, in some cases from 10 to 60 μm. For use in a bed in unsupported form the particles may have a size from about 0.1 to 0.5 mm in some instances from 0.2 to 0.4 mm.

In the present application, the feed to the oxidative dehydrogenation reactor includes oxygen in an amount below the upper explosive/flammability limit. For example for ethane oxidative dehydrogenation, typically the oxygen will be present in an amount of not less than about 16 mole % preferably about 18 mole %, for example from about 22 to 27 mole %, or 23 to 26 mole %. It is desirable not to have too great an excess of oxygen as this may reduce selectivity arising from combustion of feed or final products. Additionally, too high an excess of oxygen in the feed stream may require additional separation steps at the downstream end of the reaction.

To maintain a viable fluidized or moving bed, the mass gas flow rate through the bed must be above the minimum flow required for fluidization ($U_{mf}$), and preferably from about 1.5 to about 10 times $U_{mf}$ and more preferably from about 2 to about 6 times $U_{mf}$. $U_{mf}$ is used in the accepted form as the abbreviation for the minimum mass gas flow required to achieve fluidization, C. Y. Wen and Y. H. Yu, "Mechanics of Fluidization", Chemical Engineering Progress Symposium Series, Vol. 62, p. 100-111 (1966). Typically the superficial gas velocity required ranges from 0.3 to 5 m/s.

The reactor may also be a fixed bed reactor.

The oxidative dehydrogenation process comprises passing a mixed feed of ethane and oxygen, as described above, at a temperature up to 425° C. in some instances less than 400° C., in some instances less than 390° C., in some instances less than 380° C., in some instances as low as 375° C., in some embodiments above 365° C. at a gas hourly space velocity of not less than 500 $hr^{-1}$, typically not less than 1000 $hr^{-1}$, desirably not less than 2800 $hr^{-1}$ preferably at least 3000 $hr^{-1}$ through one or more beds and a pressure from 0.8 to 1.2 atmospheres comprising passing said mixture over the oxidative dehydrogenation catalyst. In some embodiments the oxidative dehydrogenation reactor operates at temperatures below 400° C. typically from 375° C. to 400° C.

If the composition of the reactants is below the lower flammability limit higher temperatures could be used up to about 425° C.

The outlet pressure from the reactor may be from 105 kPag (15 psig) to 172.3 kPag (25 psig) and the inlet pressure is higher by the pressure drop across the bed which depends on a number of factors including reactor configuration, particle size in the bed and the space velocity. Generally the pressure drop may be below 689 kPag (100 psig) preferably less than 206.7 kPag (30 psig).

The residence time of one or more alkanes in the oxidative dehydrogenation reactor is from 0.002 to 20 seconds.

The Support/Binder

If required there are several ways the oxidative dehydrogenation catalyst may be supported or bound.

Preferred components for forming ceramic supports and for binders include oxides of titanium, zirconium, aluminum, magnesium, silicon, phosphates, boron phosphate, zirconium phosphate and mixtures thereof, for both fluidized and fixed bed reactors. In the fluidized bed typically catalyst is generally spray dried with the binder, typically forming spherical particles ranging in size (effective diameter) from 40-100 μm. However, one needs to be careful to insure that particles area is sufficiently robust to minimize the attrition in the fluidized bed.

The support for the catalyst for the fixed bed may further be a ceramic precursor formed from oxides, dioxides, nitrides, carbides selected from the group consisting of silicon dioxide, fused silicon dioxide, aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, yttrium oxide, aluminum silicate, silicon nitride, silicon carbide and mixtures thereof.

In one embodiment, the support for the fixed bed may have a low surface area less than 20 $m^2/g$, alternatively, less than 15 $m^2/g$, in some instances, less than 3.0 $m^2/g$ for the oxidative dehydrogenation catalyst. Such support may be prepared by compression molding. At higher pressures the interstices within the ceramic precursor being compressed collapse. Depending on the pressure exerted on the support precursor the surface area of the support may be from about 20 to 10 $m^2/g$.

The low surface area support could be of any conventional shape such as spheres, rings, saddles, etc.

It is important that the support be dried prior to use (i.e. before adding catalyst). Generally, the support may be heated at a temperature of at least 200° C. for up to 24 hours, typically at a temperature from 500° C. to 800° C. for about 2 to 20 hours, preferably 4 to 10 hours. The resulting support will be free of adsorbed water and should have a surface hydroxyl content from about 0.1 to 5 mmol/g of support, preferably from 0.5 to 3 mmol/g.

The amount of the hydroxyl groups on silica may be determined according to the method disclosed by J. B. Peri and A. L. Hensley, Jr., in *J. Phys. Chem.*, 72 (8), 2926, 1968, the entire contents of which are incorporated herein by reference.

The dried support for a fixed bed catalyst may be compressed into the required shape by compression molding. Depending on the particle size of the support, it may be combined with an inert binder to hold the shape of the compressed part.

Loadings

Typically the catalyst loading on the support for a fixed bed catalyst provides from 1 to 30 weight % typically from 5 to 20 weight %, preferably from 8 to 15 weight % of said catalyst and from 99 to 70 weight %, typically from 80 to 95 weight %, preferably from 85 to 92 weight %, respectively, of said support.

The catalyst may be added to the support in any number of ways. For example the catalyst could be deposited from an aqueous slurry onto one of the surfaces of the low surface area support by impregnation, wash-coating, brushing or spraying. The catalyst could also be co-precipitated from a slurry with the ceramic precursor (e.g. alumina) to form the low surface area supported catalyst.

The catalyst loading for the fluidized bed may be chosen based on a number of factors including the volume of bed, the flow rate of alkane through the bed, energy balance in the bed, binder type, etc. For the fluidized bed catalyst loading may cover a wide range of values ranging from 10 wt % up to 90 wt %, typically above 20 wt % desirably above 35 wt %.

The process should be operated to have a conversion of ethane to ethylene of at least 90%, in some instances 95%, desirably greater than 98% and a selectivity to ethylene of not less than 95%, in some instances greater than 97%.

The Oxidative Dehydrogenation Processes

The catalyst disclosed in the present application may be used with a fluidized bed or a fixed bed exothermic reaction. The fixed bed reactor is a tubular reactor and in further embodiment the fixed bed reactor comprises multiple tubes inside a shell (e.g. a shell and tube heat exchanger type construction). In a further embodiment the fixed bed reactor may comprise a number of shells in series and/or parallel. The reactions may involve one or more dehydrogenation steps including oxidative dehydrogenation, and hydrogen transfer steps including oxidative coupling of a hydrocarbon.

Typically, these reactions are conducted at temperatures from about 375° C. up to about 410° C., at pressures from about 100 to 21,000 kPag (15 to 3,000 psig), preferably at an outlet pressure from rom 105 kPag (15 psig) to 172.3 kPag (25 psig), in the presence of an oxidative dehydrogenation catalyst. The hydrocarbon stream may contain a range of compounds including $C_{2-4}$ aliphatic hydrocarbons.

In some embodiments, the reactions include the oxidative coupling of aliphatic hydrocarbons, typically $C_{1-4}$ aliphatic hydrocarbons particularly methane (e.g. when the ethane stream contains some methane) and the oxidative dehydrogenation of $C_{2-4}$ aliphatic hydrocarbons. Such reactions may be conducted using a mixed feed of hydrocarbons, in some embodiments methane or ethane or both and oxygen in a volume ratio from 70:30 to 95:5 at a temperature less than 420° C., preferably less than 400° C. at a gas hourly space velocity of not less than 280 $hr^{-1}$, in some embodiments not less than 500 $hr^{-1}$, typically not less than 1000 $hr^{-1}$, desirably not less than 2800 $hr^{-1}$, preferably at least 3000 $hr^{-1}$, and a pressure from 0.8 to 1.2 atmospheres. Typically the process may have an overall conversion of from about 50 to about a 100%, typically from about 75 to 98% and a selectivity to ethylene of not less than 90%, in some instances not less than 95%, in further embodiments not less than 98%. In some cases the temperature upper control limit is less than about 400° C., in some embodiments less than 385° C.

The resulting product stream is treated to separate ethylene from the rest of the product stream which may also contain co-products such as acetic acid, and un-reacted feed which is recycled back to the reactor.

Separation

The product stream from the reactor should have a relatively low content of ethane less, than 20 wt %, in some cases less than 15 wt % in some cases less than 10 wt %. Additionally, the product stream should have a low content of by products such as water, carbon dioxide, and carbon monoxide, generally cumulatively in a range of less than 5, preferably less than 3 wt %.

The feed and by products may need to be separated from the product stream. Some processes may use so called dilute ethylene streams. For example if the product stream does not contain too much ethane, for example less than about 15 vol. % the stream may be used directly without further purification in a polymerization reactor such as a gas phase, slurry or solution process.

The most common technique would be to use a cryogenic C2 splitter. Other known ethylene/ethane separation techniques could also be used including adsorption (oil, ionic liquids and zeolite).

The present invention will now be illustrated by the following non limiting examples.

In the examples the fixed bed reactor unit used for the oxidative dehydrogenation reaction is schematically shown in FIG. 1. The reactor was a fixed bed stainless steel tube reactor having a 2 mm (¾") outer diameter and a length of 117 cm (46 inches). The reactor is in an electrical furnace sealed with ceramic insulating material. There are 7 thermocouples in the reactor indicated at numbers 1 through 7. Thermocouples are used to monitor the temperature in that zone of the reactor. Thermocouples 3 and 4 are also used to control the heating of the reactor bed. The feed flows from the top to the bottom of the reactor. At the inlet there is a ceramic cup 8 to prevent air drafts in the reactor. Below the ceramic cup is a layer of quartz wool 9. Below the layer of quartz wool is a layer of catalytically inert quartz powder. Below the quarts powder is the fixed bed 10 comprising catalyst. Below the fixed bed is a layer of quartz powder 11, a layer of quartz wool 12 and a ceramic cup 13. At the exit of the bed was a gas analyzer to determine the composition of the product stream. The GHSV was 2685 $hr^{-1}$ and the pressure was ambient.

For the examples the bed temperature was taken as an average of the temperatures from thermocouples 2, 3 and 4. The feed stream was assumed to have the same temperature as the bed.

Comparative Example 1—Base Line (No Peroxide Treatment)

Preparation of Baseline:
  100 g reaction in glass lined PARR® autoclave
Procedure:
  96.00 g of $(NH_4)_6Mo_6TeO_{2x}7H_2O$ (s) was dissolved in 300 mL of de-ionized water in a 1 L three neck round bottom flask (RBF), with a stir rate of 750 rpm with the addition of a warm water bath
  70.22 g of $VOSO_4 \times 3.41H_2O$ (s) was dissolved in 100 mL of de-ionized water, with the addition of a warm water bath
  194.35 g of $H_3[NbO(C_2O_4)_3]$ (soln.) was weighed into a 250 mL beaker and held for later use
  $VOSO_4 \times 3.41H_2O$ (aq) solution was added to the $(NH_4)_6Mo_6TeO_{2x}7H_2O$ (aq) solution in the 1 L RBF
  Solution turned black
  Solution was left to stir for 30 minutes, after which the solution turned a purple color All manipulations were performed in air 194.35 g of $H_3[NbO(C_2O_4)_3]$ (soln.) was added to a 250 mL addition funnel, affixed to the 3 neck RBF Solution was added dropwise to the agitating purple slurry (15 minutes for addition time)

Solution remained as a dark purple slurry

Solution was transferred to a 1 L glass liner inside a 1 L PARR autoclave

Autoclave set up was sealed and purged 10 times with repeating N2 (g) evacuation sequences Autoclave was connected to the condenser set up Reaction was left to stir overnight in the autoclave set up at room temperature The following day the PARR autoclave was heated to 175° C., the autoclave reached a temperature of 172° C. after 7.5 hours Reaction mixture was left to heat in the autoclave set up overnight at 175° C. with the condenser set up The following day the temperature was set back to room temperature Reaction set up was not cooled by the end of the day and was left to cool over the weekend After the reaction was cooled it was depressurized and filtered through 4× WHATMANN #4 filter paper media The filter cake was rinsed with approximately 0.5 L of deionized water until the filtrate ran clear Filtration time was approximately 2 hours Filter dried catalyst was dried in the oven at 90° C. overnight Dried catalyst was ground and sieved Yield: 111 g 7 g of the 111 g was calcined under N2 (g)

Figure 2:
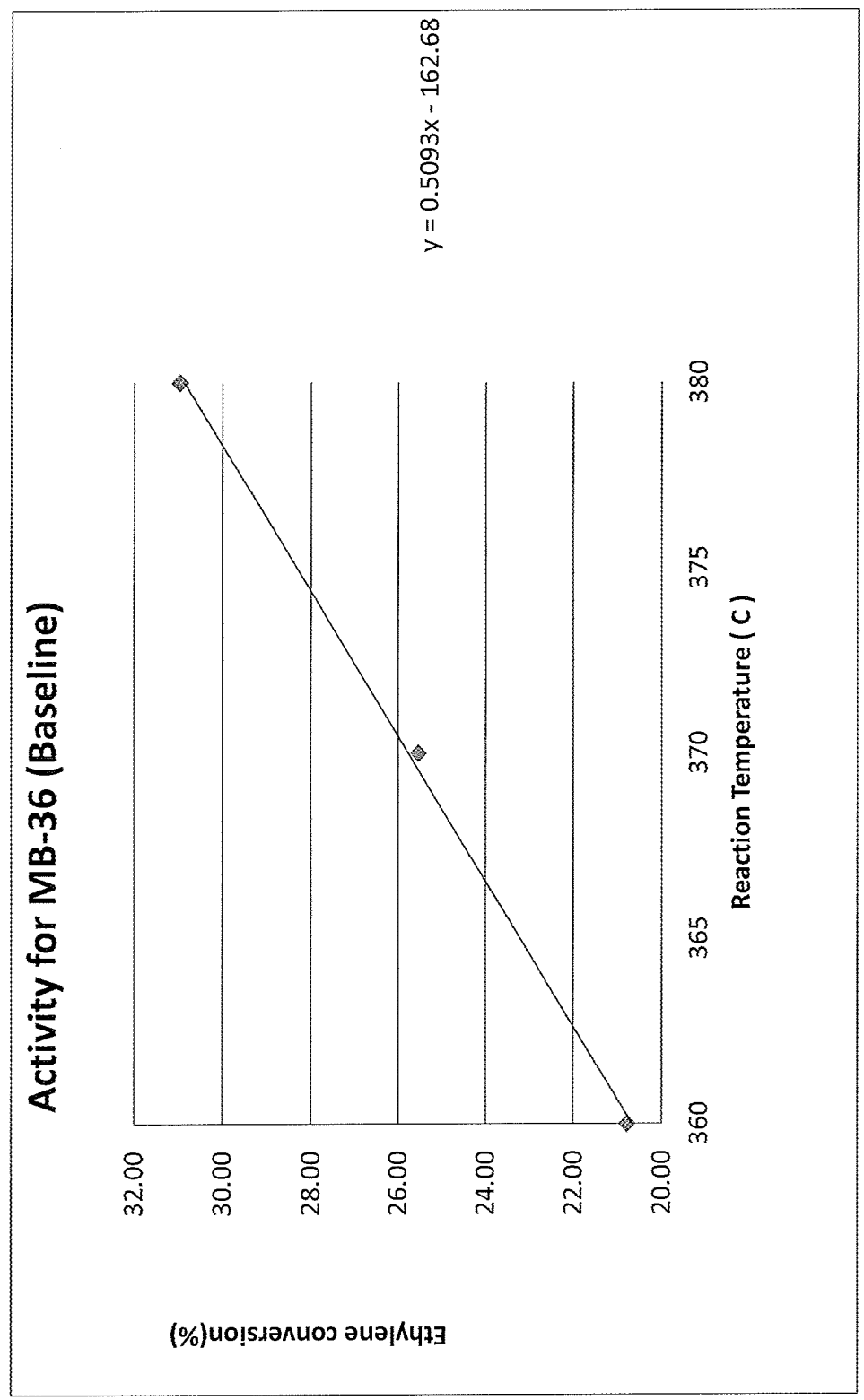
FIG. 2 is plot of the conversion of ethylene as a function of temperature for a catalyst prepared without $H_2O_2$ treatment.
Figure 3:
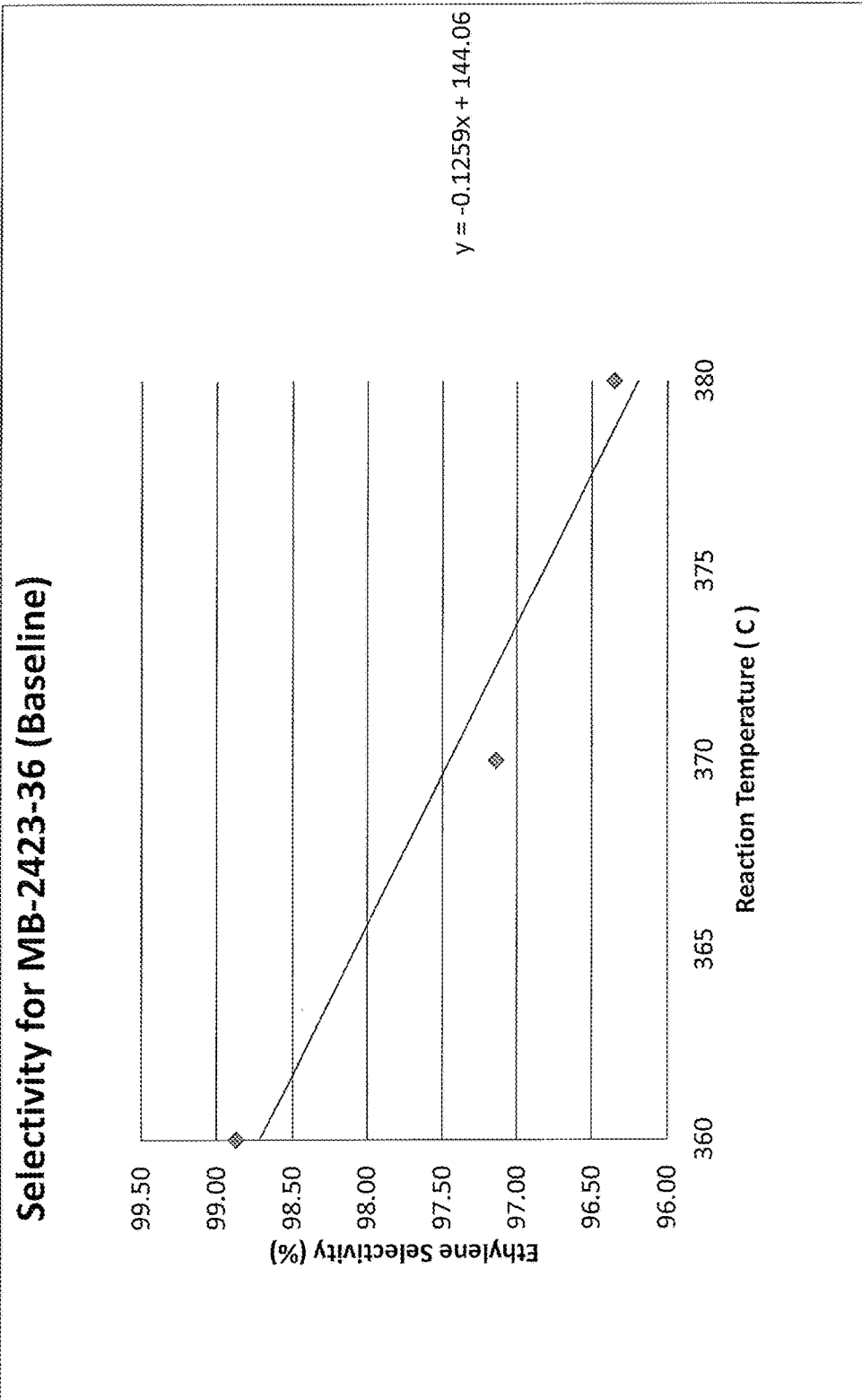
FIG. 3 is a plot of selectivity for ethylene against temperature for a catalyst prepared without $H_2O_2$ treatment.

Activity Testing:

7 grams of calcined catalyst were loaded into the reactor shown in FIG. 1. Ethane and oxygen were passed through the reactor at a rate of 140 sccm per minute at various temperatures and the conversion and selectivity to ethylene at various temperatures were recorded. A plot was made of the conversion and activity of the catalyst at various temperatures. These are shown in FIGS. 2 and 3 respectively.

From the plots the temperature at which 25% conversion of ethane was obtained was 368.5° C. At this temperature the conversions to ethylene was 97.7%.

Comparative Example 2—Catalyst Treated Once with $H_2O_2$

Procedure:

To a 1 L 2 neck round bottom flask was charged 10.2544 g of uncalcined base catalyst from experiment 1.

To this black/purple catalyst mixture was charged 35 mL of distilled deionized water Catalyst/water mixture began to bubble and fizz upon the addition of water The catalyst/water mixture was agitated at 400 rpm to produce a thin slurry 7.14 mL of 30% $H_2O_2$ was charged to the 1 L 2 neck round bottom flask The catalyst, $H_2O_2$ mixture was agitated at 400 rpm The reaction began to bubble and the purple/black slurry turned into a dark brown slurry Mixture was left to stir until bubbling subsided and reaction flask cooled to touch (approximately 2 hours)

Mixture was filtered through a Buchner funnel with 3× WHATMANN #4 filter paper

Catalyst/$H_2O_2$ solid was dried in a vacuum oven at 90° C. under ambient pressure for 12 hours Catalyst was cooled to touch, ground, sieved and calcined Repeat:

The above procedure was repeated using 5.29 g of uncalcined base catalyst.

Figure 4:
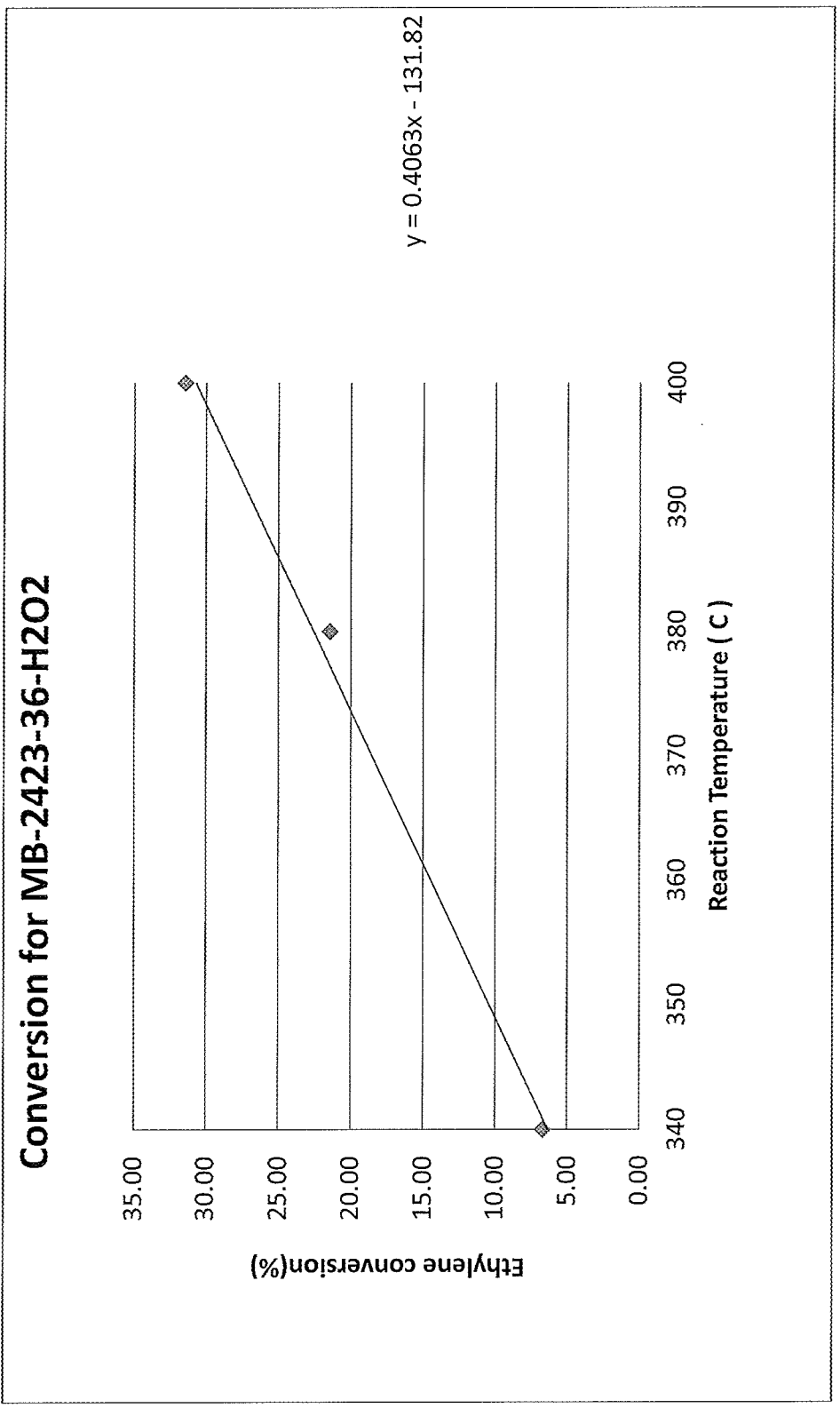
FIG. 4 is a plot of the conversion of ethylene as a function of temperature for a catalyst prepared only treating the precursor with $H_2O_2$.
Figure 5:
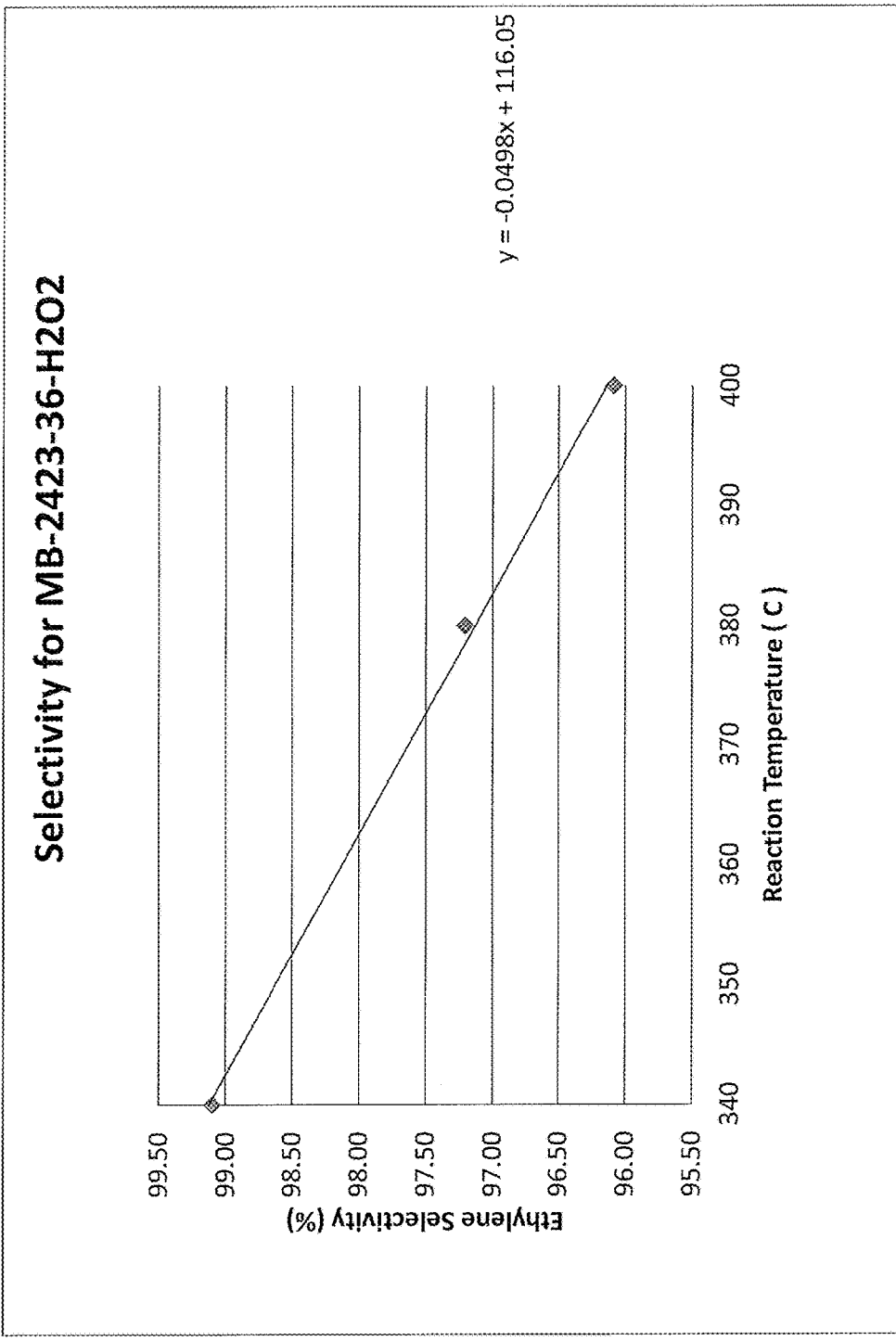
FIG. 5 is a plot of the selectivity for ethylene against temperature for a catalyst in which only the precursor was treated with $H_2O_2$.

Samples of the calcined catalysts were tested as above. A plot was made of the conversion and activity of the catalyst at various temperatures. These are shown in FIGS. 4 and 5 respectively.

From the plots the temperature at which 25% conversion of ethane was obtained was 386.0° C. At this temperature the conversions to ethylene was 96.8%

Example 3 (Non Limiting Example of this Invention)

Procedure:

To a 2 L 3 neck round bottom flask was charged 5.2934 g of ODH catalyst of example 2 ($H_2O_2$ treatment before calcining)

20 mL of distilled, deionized water was then charged into the 2 L 3 neck RBF

Figure 6:
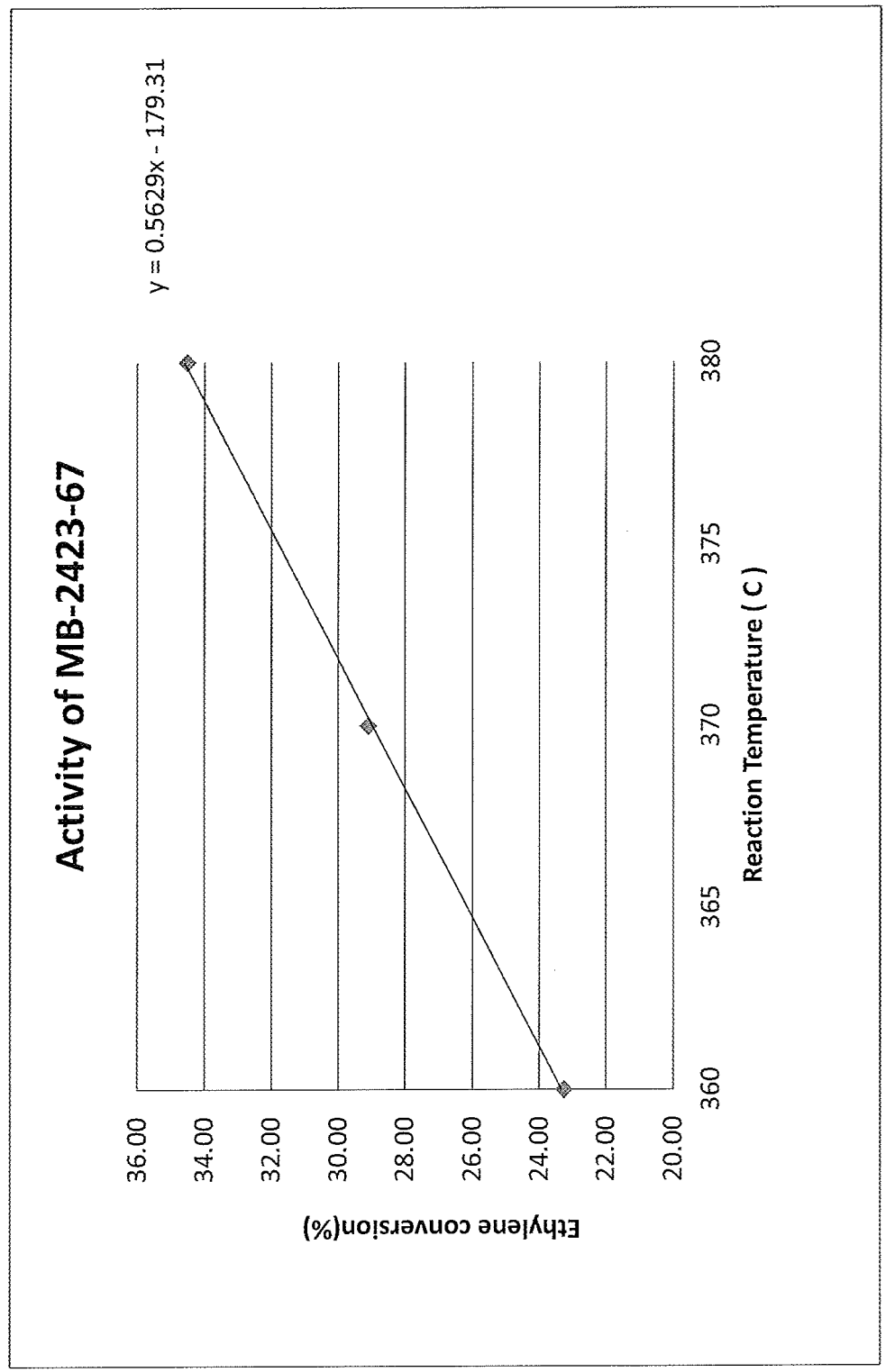
FIG. 6 is a plot of the conversion of ethylene as a function of temperature for a catalyst prepared according to the present disclosure.
Figure 7:
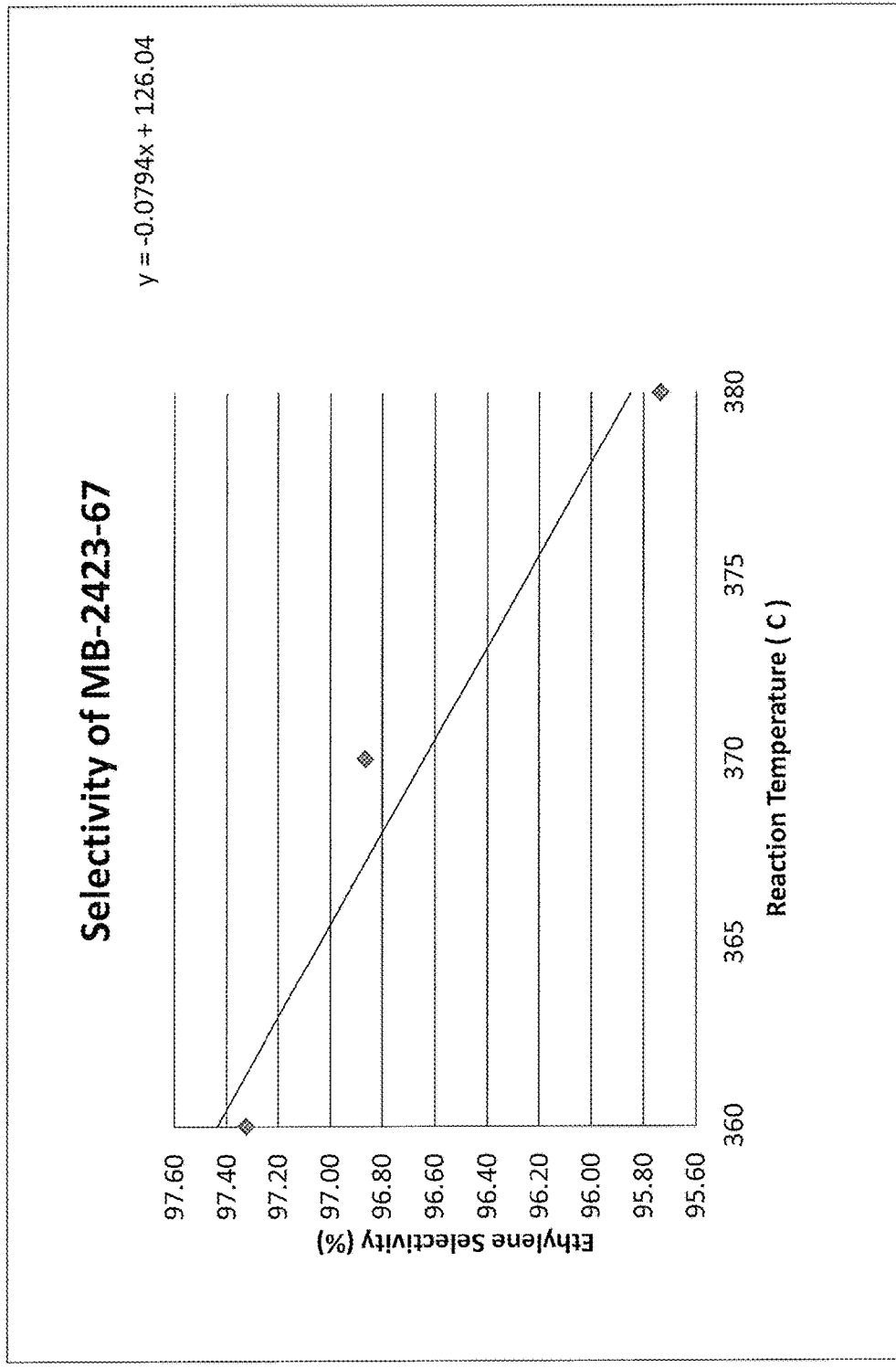
FIG. 7 is a plot of the selectivity for ethylene against temperature for the catalyst of the present disclosure.

The black catalyst bubbled during the addition of the distilled, deionized water addition 3.78 mL of 30% $H_2O_2$ was charged into the 3 neck round bottom flask The slurry mixture bubbled and fizzed during the addition of the 30% $H_2O_2$ The slurry mixture was agitated at room temperature at 350 rpm for 3 hours Mixture was stopped from stirring and filtered using a Buchner funnel with 3× WHATMANN #4 filter papers The dark purple/black solid was dried in a vacuum oven at 90° C. ambient pressure The solids were cooled to room temperature, ground, sieved About a 2 g (±0.5) sample of the twice treated catalyst was tested in the reactor as in example 1. The plots are shown in FIGS. 6 and 7.

From the plots the temperature at which 25% conversion of ethane was obtained was 363.0° C. At this temperature the conversions to ethylene was 97.2%.

Figure 8:
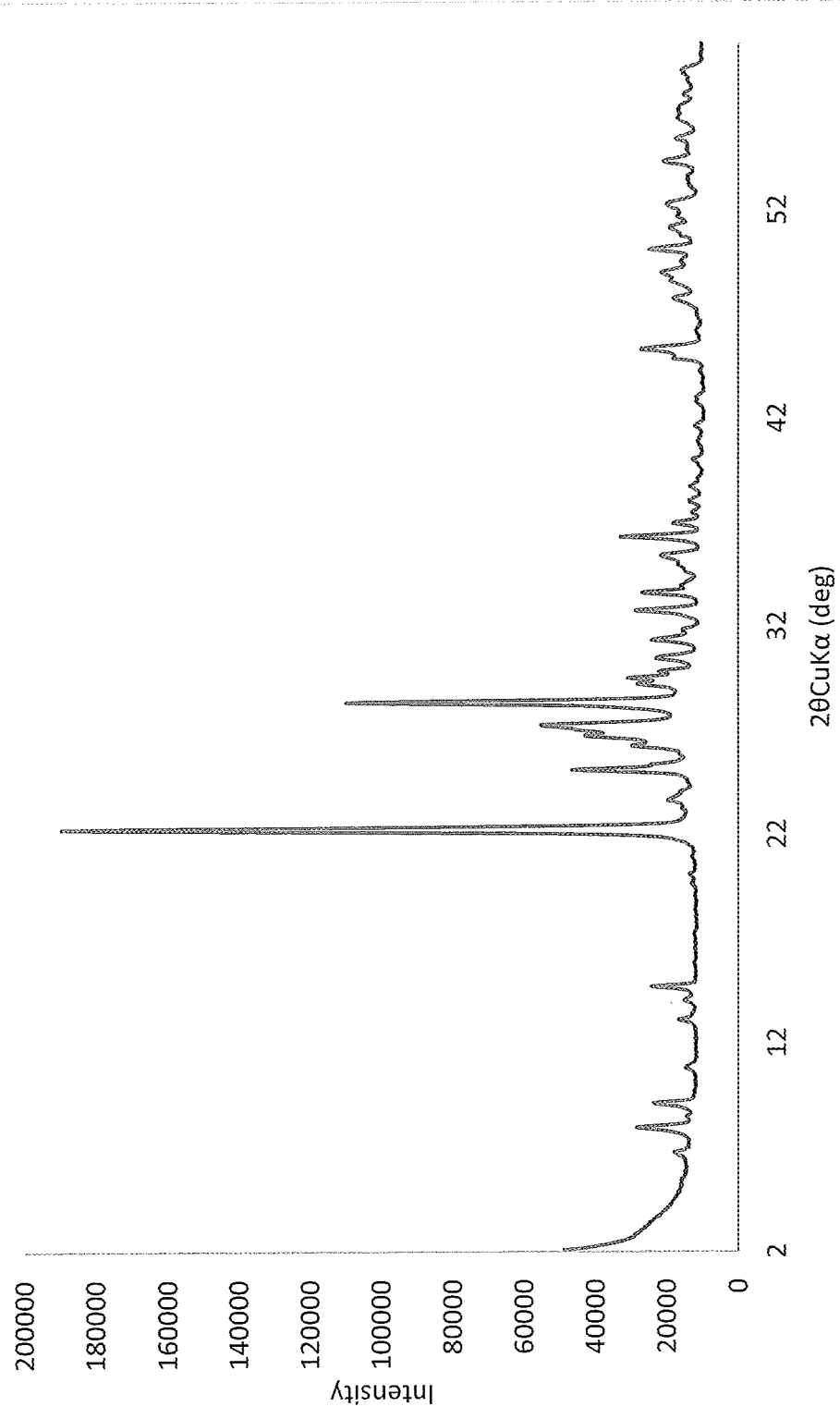
FIG. 8 is an XRD diffraction pattern (collected with $Cu_{K\alpha}$ source) of the catalyst prepared according to comparative example 1.
Figure 9:
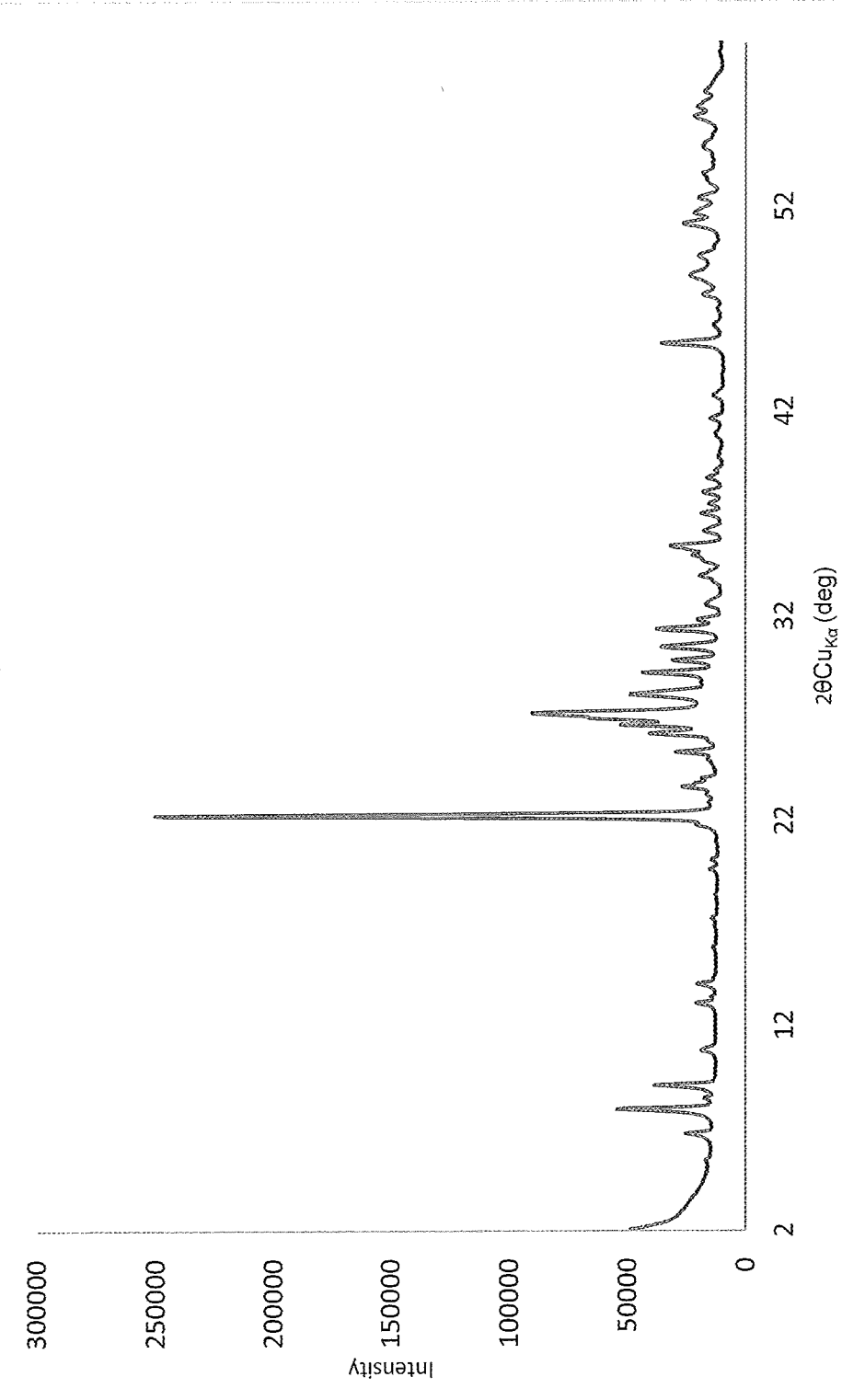
FIG. 9 is an XRD diffraction pattern (collected with $Cu_{K\alpha}$ source) of the catalyst prepared according to example 3.
Figure 10:
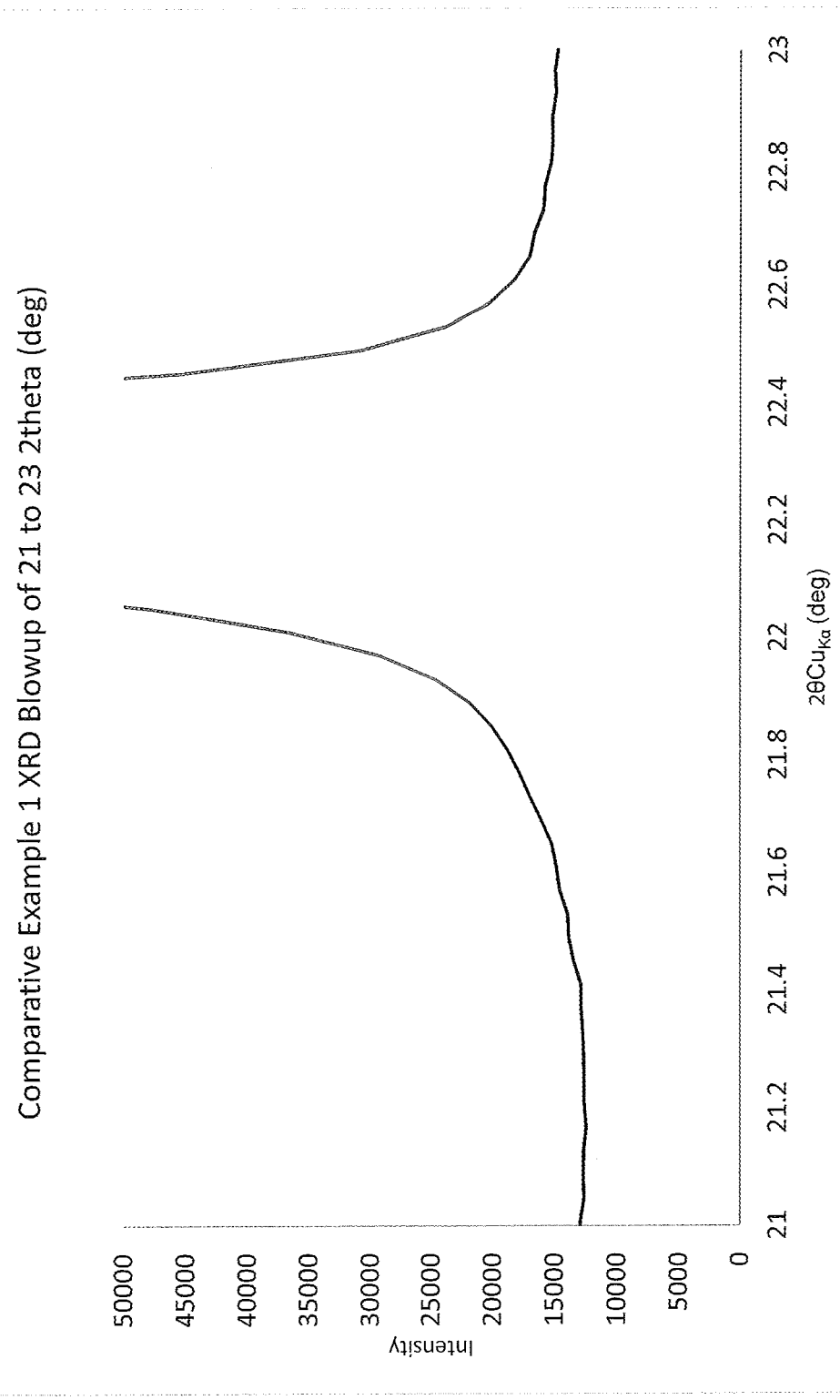
FIG. 10 is a blow up of the XRD diffraction pattern ($Cu_{K\alpha}$ source) of the catalyst prepared according to comparative example 1, between 21 and 23 twoφ.
Figure 11:
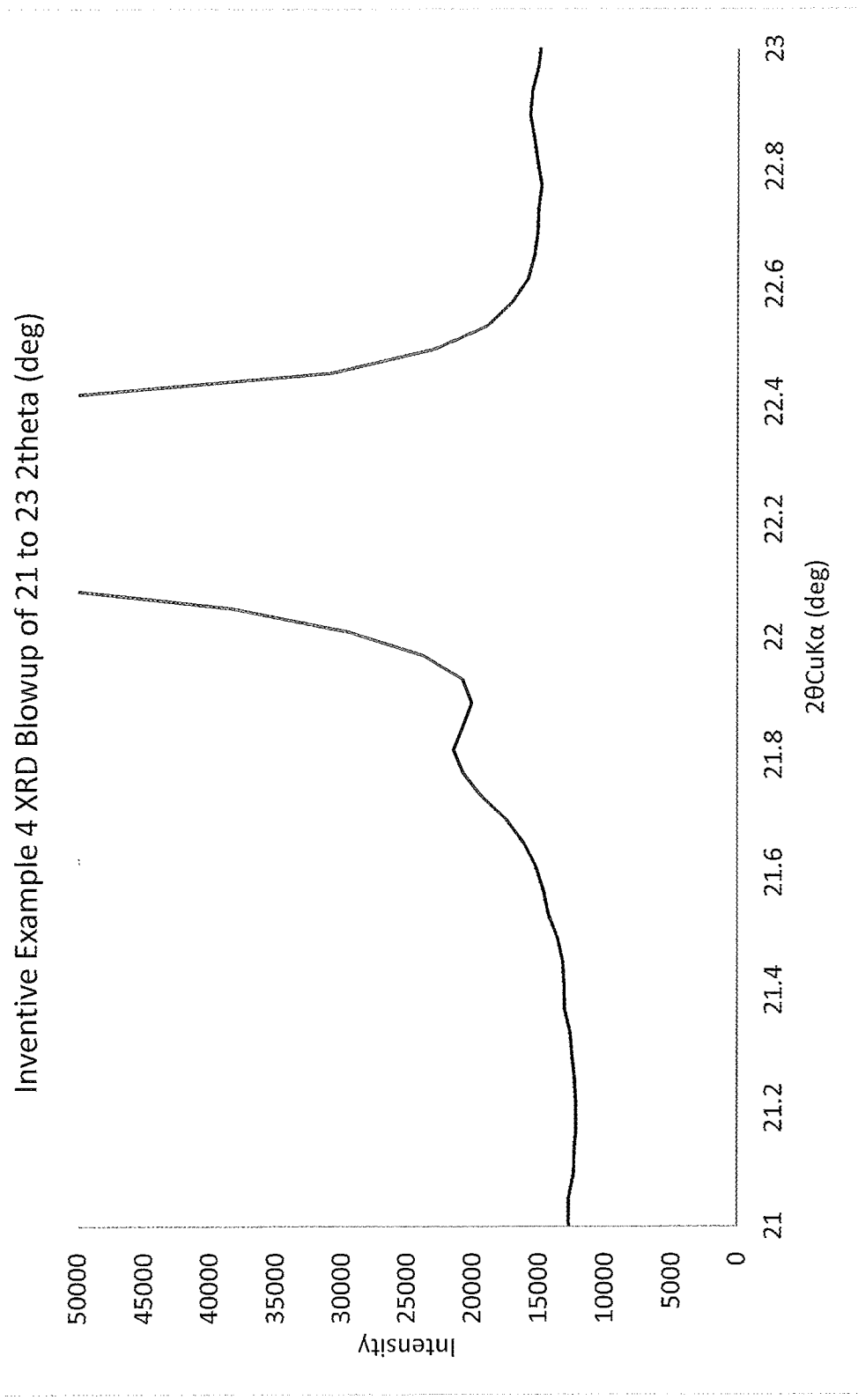
FIG. 11 is a blow up of the XRD ($Cu_{K\alpha}$ source) diffraction pattern of the catalyst prepared according to example 3, between 21 and 23 twoφ).

XRD diffraction patterns were taken for the catalyst made according to comparative example 1 and example 3. These are FIGS. 8 and 9. A blow up of the portions of XRD patterns between 21 and 23, 2 ϕ are shown as FIGS. 10 and 11 respectively.

The present disclosure has shown that when a MoVNb-TeO$_x$ catalyst with already high performance is treated both before and after calcination, the resulting catalyst has high activity which is improved relative to the non-treated baseline, whereas with the single treatment method (before calcination) the catalyst activity has decreased reactivity relative to the non-treated baseline. Additionally, washing with hydrogen peroxide twice increases the intensity of a reflection at 21.7 2θ in the X-ray powder diffraction (XRD) relative the baseline catalyst A chart of XRD diffraction pattern data for the experiments and prior art data was prepared.

| 2θCuKα (deg) | Comparative Example 1 (Baseline) Relative Intensities (%) to 22.29* (±0.4°) 2θ (deg) | Comparative Example 2 (1x $H_2O_2$ treatment) Relative Intensities (%) to 22.29 (±0.4°) 2θ (deg) | Inventive Example 3 (2x $H_2O_2$ treatment) Relative Intensities (%) to 22.29 (±0.4°) 2θ (deg) | Mitsubishi Claimed JP 3484729 (B2) 2θ (deg) | Relative Intensities (%) to 22.1* (±0.4°) 2θ (deg) | Nieto Claimed ES 2428442 US 2014011410 WO 2014062046 2θ (deg) | Relative Intensities (%) to 22.1* (±0.4°) 2θ (deg) |
|---|---|---|---|---|---|---|---|
| 6.77 (±0.4) | 2 | 5 | 4 | | | | |
| 7.97 (±0.4) | 9 | 18 | 16 | | | 7.7 (±0.4) | 10 to 40 |
| 9.13 (±0.4) | 6 | 11 | 10 | | | 8.9 (±0.4) | 10 to 40 |
| 10.81 (±0.4) | 2 | 3 | 3 | | | | |
| 13.13 (±0.4) | 3 | 5 | 3 | | | | |
| 14.05 (±0.4) | 2 | 4 | 3 | | | | |
| 14.73 (±0.4) | 7 | 0 | 0 | | | | |
| 21.81 (±0.4) | 4 | 4 | 4 | | | | |
| 22.29* (±0.4) | 100 | 100 | 100 | 22.1* (±0.4) | 100 | 22.1* (±0.4) | 100 |
| 23.65 (±0.4) | 4 | 6 | 7 | | | | |
| 25.13 (±0.4) | 19 | 2 | 2 | | | | |
| 26.29 (±0.4) | 10 | 13 | 12 | | | 26.1 (±0.4) | 10 to 90 |
| 26.73 (±0.4) | 17 | 17 | 18 | | | 26.9 (±0.4) | 20 to 80 |
| 27.05 (±0.4) | 19 | 26 | 23 | | | | |
| 27.29 (±0.4) | 24 | 33 | 33 | | | 27.1 (±0.4) | 20 to 120* |
| 28.21 (±0.4) | 20 | 17 | 16 | 28.2 (±0.4) | 400~3 | 28.1 (±0.4) | 20 to 120* |
| 29.29 (±0.4) | 9 | 13 | 12 | | | | |
| 29.57 (±0.4) | 10 | 2 | 2 | | | | |
| 29.85 (±0.4) | 6 | 8 | 9 | | | | |
| 30.53 (±0.4) | 6 | 11 | 11 | | | | |
| 31.37 (±0.4) | 7 | 10 | 12 | | | 31.2 (±0.4) | 10 to 90 |
| 31.85 (±0.4) | 2 | 4 | 4 | | | | |
| 32.81 (±0.4) | 10 | 2 | 2 | | | | |
| 33.65 (±0.4) | 9 | 1 | 1 | | | | |
| 35.45 (±0.4) | 6 | 9 | 9 | | | 35 (±0.4) | 10 to 90 |
| 36.33 (±0.4) | 13 | 3 | 2 | 36.2 (±0.4) | 80~3 | | |
| 37.01 (±0.4) | 4 | 3 | 4 | | | | |
| 44.89 (±0.4) | 5 | 1 | 1 | | | | |
| 45.33 (±0.4) | 10 | 10 | 11 | 45.1 (±0.4) | 40~3 | 45.06 | 10 to 60 |
| 47.81 (±0.4) | 5 | 3 | 4 | | | | |
| 51.21 (±0.4) | 5 | 7 | 8 | 50 | 50~3 | | |
| 51.73 (±0.4) | 4 | 5 | 6 | | | | |
| 52.45 (±0.4) | 5 | 4 | 5 | | | | |

What is claimed is:

1. A method to improve the consistency of an oxidative dehydrogenation catalyst of the empirical formula (measured by PIXE): $Mo_{1.0}V_{0.25-0.38}Te_{0.10-0.16}Nb_{0.15-0.19}O_d$ where d is a number to satisfy the valence of the oxide; the method comprising preparing the oxidative dehydration catalyst by:
   i) forming an aqueous solution of ammonium heptamolybdate (tetrahydrate) and telluric acid at a temperature from 30° C. to 85° C. and adjusting the pH of the solution to from 6.5 to 8.5, with a nitrogen-containing base to form soluble salts of the metals;
   ii) preparing an aqueous solution of vanadyl sulphate at a temperature from room temperature to 80° C.;
   iii) mixing the solutions from steps i) and ii) together;
   iv) slowly (dropwise) adding a solution of niobium monoxide oxalate ($NbO(C_2O_4H)_3$) to the solution of step iii) to form a slurry;
   v) heating the resulting slurry in an autoclave under an inert atmosphere at a temperature from 150° C. to 190° C. for not less than 10 hours;
   vi) filtering and washing with deionized water, and drying the washed solid from step v) for a time from 4 to 10 hours at a temperature from 70 to 100° C. to form a dried catalyst precursor;
   vii) treating said dried catalyst precursor from step vi) with the equivalent of from 0.3-2.8 mL of a 30% w/w solution of $H_2O_2$ per gram of said dried catalyst precursor for a time from 5 minutes to 10 hours at a temperature from 20 to 80° C.;
   viii) calcining the resulting catalyst precursor in an inert atmosphere at a temperature from 200° C. to 600° C. for a time from 1 to 20 hours to form a calcined catalyst;
   ix) recovering the calcined catalyst from step viii) and treating it with the equivalent of from 0.3-2.8 mL of a 30% w/w solution of $H_2O_2$ per gram of calcined catalyst for a time from 5 minutes to 10 hours at a temperature from 20 to 80° C.; and
   x) recovering the treated calcined catalyst to provide the oxidative dehydration catalyst.

2. The method according to claim 1, wherein in the catalyst the molar ratio of Mo:V is from 1:0.26 to 1:0.38.

3. The method according to claim 2, wherein in the catalyst the molar ratio of Mo:Te is greater than 1:0.11 and less than 1:0.15.

4. The method according to claim 3, wherein in the catalyst the molar ratio of Mo:Te is from 1:0.11 to 1:0.13.

5. The method according to claim 1, wherein the catalyst has a bulk density from 1.20 to 1.53 g/cc.

6. The method according to claim 1, wherein in the crystalline phase of the catalyst the amount of the phase having the formula $(TeO)_{0.39}(Mo_{3.52}V_{1.06}Nb_{0.42})O_{14}$ is above 75 wt % of the measured crystalline phase.

7. The method according to claim 1, wherein the catalyst has an XRD diffraction pattern (reflections data) where the reflection at 21.81° (±−0.4°) 2θ is 1-6% relative peak height of the reference reflection at 22.29° (±0.4°) 2θ.

8. The method according to claim 1, wherein the catalyst has an XRD pattern where the reflection at 22.29° (±0.4°) 2θ has a full width at half maximum (FWHM) less than 0.185° 2θ.

9. The method according to claim 1, wherein the surface of the autoclave is selected from the group consisting of stainless steel, silica, glass (PYREX), alumina coating and polytetrafluoroethylene.

10. The method according to claim 1, wherein the autoclave contains particulates (irregular such as flakes, granules, globules, filaments etc. or regular such as spheres, elliptical, rods, rectangular prisms (both right and non-right), pentagonal prisms, pyramids, etc.) of stainless steel, silica, alumina and polytetrafluoroethylene seeded with the above catalyst.

11. The method according to claim 1, the autoclave is internally coated with a fully fluorinated ethylene propylene polymer reactor seeded with the catalyst.

* * * * *